US00PP12204P2

(12) United States Plant Patent
Smith

(10) Patent No.: US PP12,204 P2
(45) Date of Patent: Nov. 13, 2001

(54) *MAGNOLIA VIRGINIANA* NAMED 'MATTIE MAE SMITH'

(75) Inventor: John Allen Smith, Chunchula, AL (US)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 09/358,573

(22) Filed: Jul. 12, 1999

(51) Int. Cl.[7] ..... A01H 5/00
(52) U.S. Cl. ..... Plt./223
(58) Field of Search ..... Plt./223

(56) References Cited

U.S. PATENT DOCUMENTS

P.P. 11,029 * 8/1999 Sallin ..... Plt./223

* cited by examiner

*Primary Examiner*—Bruce R. Campbell
*Assistant Examiner*—Wendy C Baker
(74) *Attorney, Agent, or Firm*—Christie, Parker & Hale, LLP

(57) ABSTRACT

A new and distinct plant variety of *Magnolia virginiana* var. *australis* characterized by its distinctive variegated foliage.

2 Drawing Sheets

BACKGROUND OF THE INVENTION

The present invention relates to a new and distinct variety of *Magnolia virginiana* var. *australis* and was discovered as a seedling variant in a cultivated area of a nursery located near Chunchulla, Ala., by the originator, Mr. John Allen Smith. The plant was discovered in 1995 and grown near Chunchulla, Ala. since the discovery. The varietal denomination of the new variety is 'Mattie Mae Smith'.

The genus Magnolia is included in the family Magnoliaceae that comprises about 12 genera of deciduous and evergreen trees and shrubs, native mostly to temperate regions of the Northern Hemisphere, extending into the Americas and Asiatic tropics. The genus Magnolia, comprising 85 or more species, is widespread in Asia from the Himalayas to Japan and in America from eastern North America to Central America and Venezuela. Magnolia includes many highly ornamental trees and shrubs prized by gardeners in temperature to tropical zones. *Magnolia virginiana* is an abundant shrub or tree in eastern North America from Massachusetts to Florida, especially along the coast. The southern race of *Magnolia virginiana* is designated var. *australis* primarily on the basis of the evergreen character of its foliage. It is abundant from Georgia south to Florida and Alabama.

SUMMARY OF THE INVENTION

The cultivar is a chance seedling resulting from a collection of fruits obtained from a wild tree thought to have been growing in or near Alachua County, Fla. This location is near 30 degrees north latitude and is in USDA plant hardiness zone 8b. This zone has a mean annual minimum temperature for the period of record of 15° F. to 20° F. (−9.5° C. to −6.6° C.).

The natural *Magnolia virginiana* is a tall evergreen, more or less upright tree, reaching 30 meters tall and 1 meter in diameter in undisturbed natural stands. The species habitat is swamps, bogs, bays, wet ravines and wet flatlands within its range, extending from approximately mid-Alabama, mid-Georgia and mid-South Carolina in the north to lower peninsular Florida in the south.

Below is a detailed description of the new selection of *Magnolia virginiana*, 'Mattie Mae Smith':

Mature leaves are prominently variegated, waxy, shiny above, with contrasting deep green tissue, color 139A, and pale yellow to olive-green tissue, color 144A. Mature leaves are leathery, with petioles up to 3 cm long, oblong lanceolate to ovate lanceolate.

Asexual reproduction of the new variety by stem cutting performed near Chunchulla, Ala., has confirmed that the distinctive characteristics of the new variety are stable and transmitted to succeeding generations.

COMPARISON WITH PARENTS

'Mattie Mae Smith' is distinguished from its parents and all other varieties of *Magnolia virginiana* var. *australis* of which I am aware by the distinctive variegation of its foliage.

DESCRIPTION OF ILLUSTRATIONS

The accompanying photographic illustrations show a specimen of the new cultivar as true to color as is reasonably possible to make in an illustration of this character.

DETAILED DESCRIPTION OF THE NEW VARIETY

Figure 1:
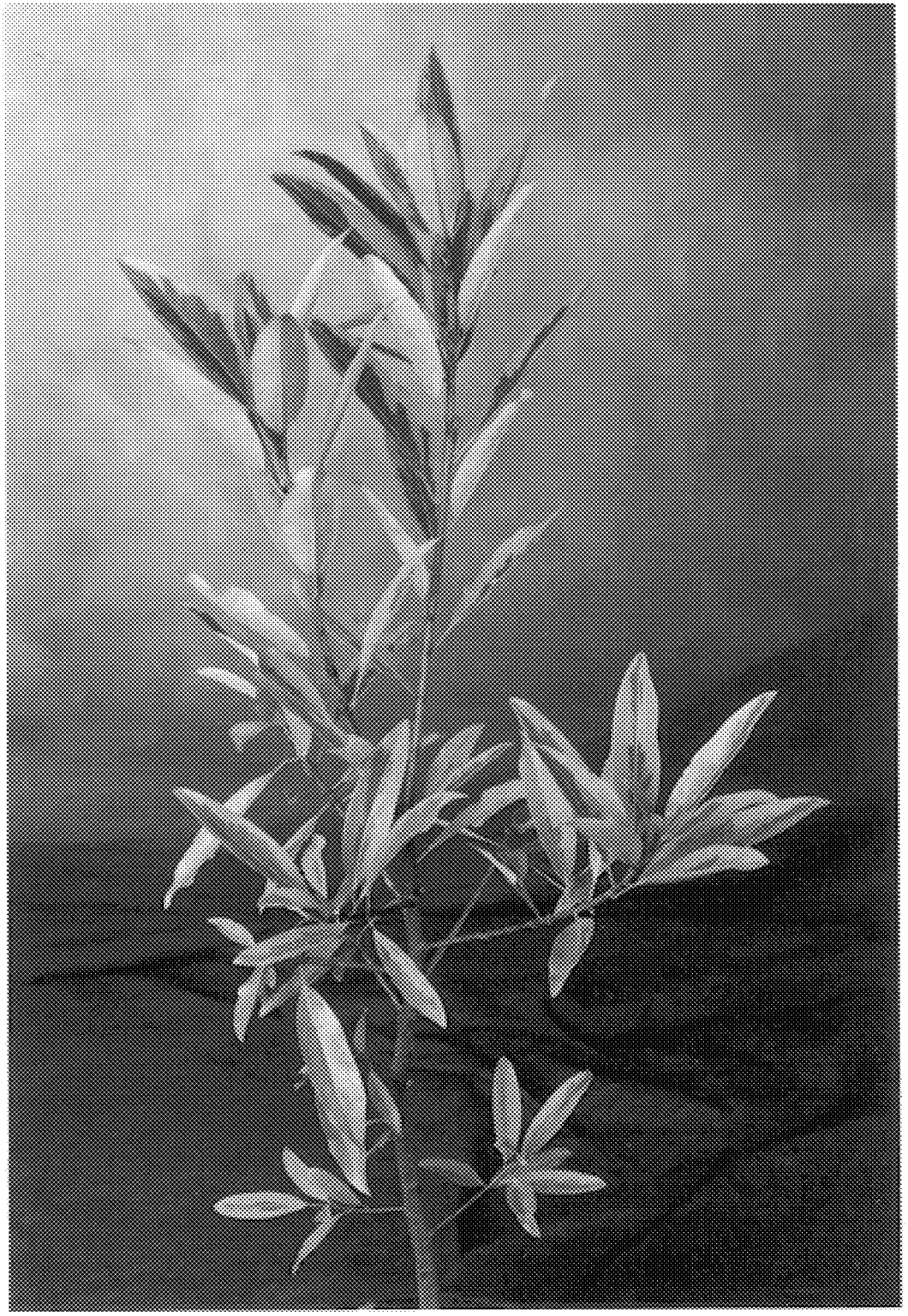
FIG. 1 illustrates a 3-year-old specimen of the new variety.
Figure 2:
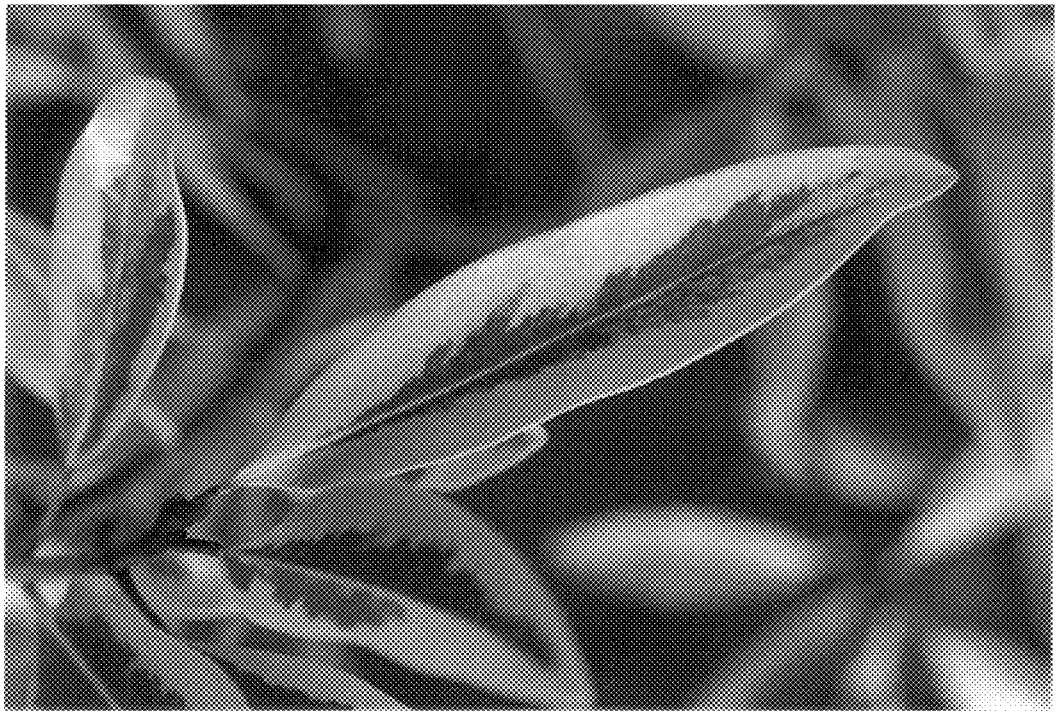
FIG. 2 illustrates the distinctive variegated foliage of the new variety.
Figure 3:
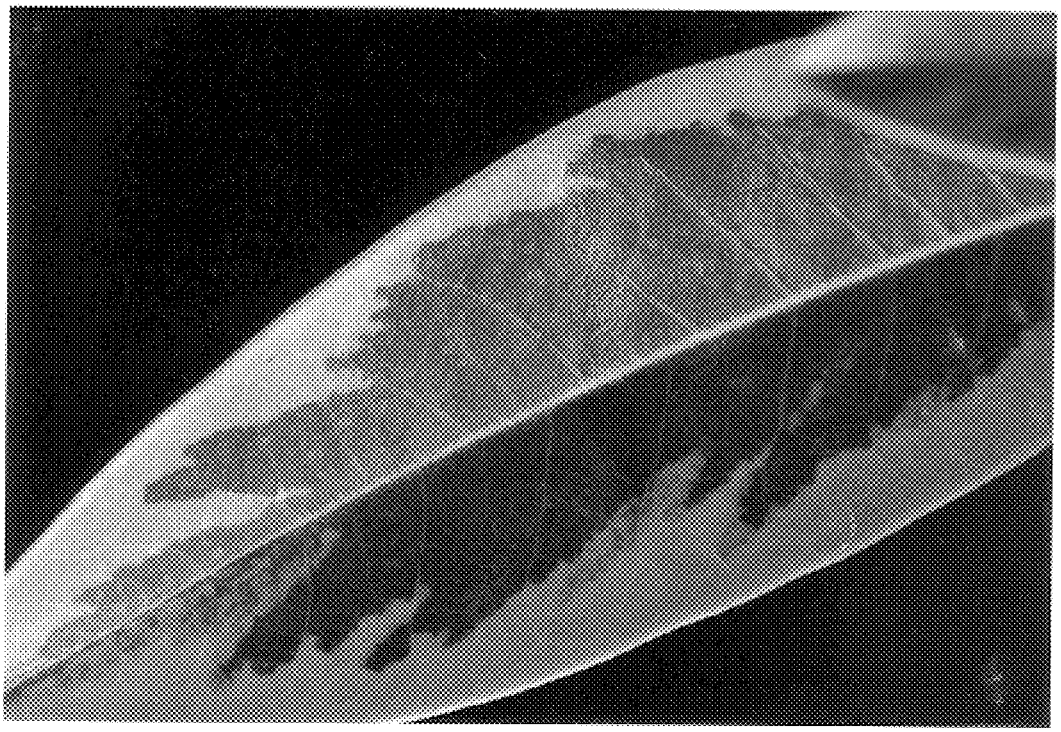
FIG. 3 is a close-up of a leaf.

*Magnolia virginiana* var. *australis* 'Mattie Mae Smith' has not been observed under all possible environmental, cultural, and light conditions. The following observations and descriptions are of 3 year-old plants grown in Mobile County, Ala., and in other locations as noted. Phenotypic expression may vary with light intensity, cultural, and environmental conditions. In this description, color references are to The Royal Horticultural Society Colour Chart (1995) and terminology used in the color descriptions herein refers to plate numbers in this color chart.

Classification:

*Botanical.*—*Magnolia virginiana* var. *australis* 'Mattie Mae Smith'.

*Parentage.*—Chance seedling of *Magnolia virginiana* var. *australis.*

*Propagation.*—By vegetative cuttings.

Plant:

*Size.*—Approximately 8 ft high and 4 ft wide (5-year-old specimen; size at maturity not yet known).

*Branching.*—Alternate; 3 or occasionally more twigs clustered in a false whorl at the ends of branches.

*Branch texture.*—Ends of young twigs silvery, silky pubescent, quickly maturing to shiny, perfectly smooth texture.

*Habit.*—Upright, single-trunked tree when young, twice as tall as wide; mature habit not yet observed.

*Leaf shape.*—Oblong-lanceolate to ovate-lanceolate; acute bases; narrow, rounded tips.

*Leaf margin.*—Entire.

*Leaf texture/substance.*—Waxy, leathery.

*Leaf variegation.*—Variegated in the form of irregular, asymmetrical central blotches, varying greatly from leaf to leaf, but typically running nearly the full length of the leaf, starting at the midrib but usually not reaching the leaf margin; the background color is dark green; variegation is light olive green; the variegation covers approximately 50% of the leaf surface.

The following Color Readings are of 5-year-old specimens in Vacaville, Calif., May 2001.

Young leaves:

*Upper side.*—Background color near Green Group 139A; marginal variegation near Yellow-Green Group 144C.

*Under side.*—Near Greyed-Green Group 193B.

Mature leaves:

*Upper side.*—Background color near Green Group 139A; marginal variegation near Yellow-Green Group 151C.

*Under side.*—Dull silvery-gray, near Greyed-Green Group 192B.

Petioles: Up to 3 cm in length

Internodes: Highly variable in young plants depending on culture, ranging from 1 cm to 15 cm in young plants observed to date; internode length on mature plants not yet observed.

Leaf size: Between 13 and 15 cm long and 4 to 5 cm wide at their broadest points.

The following Color Readings are of 5-year-old specimens in Lewisberry, Pa., April 2001.

Bark: (Oldest specimens are only 6-years old, so no observations have yet been made; color and texture of more mature specimens is not expected to differ significantly from smooth, gray-colored bark of species.)

*Texture.*—Smooth.

*Color.*—1$^{st}$ & 2$^{nd}$ year stems: From near Yellow-Green Group 146B to near Yellow-Green Group 151B, depending on exposure to sun. 3$^{rd}$ year and older growth: Near Greyed-Green Group 197B.

*Lenticels.*—A few scattered lenticels observed on older branches; oval shaped, two-lobed, with horizontal orientation; about 1 mm wide, occasionally larger.

*Hardiness.*—USDA Zone 5 to 9 (−20 F. to −10° F.).

*Disease/pests.*—No susceptibility to diseases/pests noted; no resistance to diseases/pests noted beyound resistance typical of the species.

The following Color Readings are of 5-year-old specimens in Vacaville, Calif., May 2001.

Infloresence:

*Bloom period.*—Late April / Early May for approximately 4 weeks (for specimens in Vacaville, Calif.

*Flower form.*—Ovate in bud, usually with about 9 or 10 petals, becoming nearly globose and finally salviform as the flower ages.

*Flower arrangement.*—Solitary, at the terminals of the previous year's twigs.

*Flower size.*—In bud just at anthesis, 4.0 cm to 4.5 cm long and 2.0 to 2.5 cm wide; at maturity, about 3.0 cm to 4.0 cm long and 7.0 to 8.0 cm wide just before the tepals are lost.

*Shape of infloresence.*—Solitary flowers only.

*Frangrance.*—Light to intense, sweet, with strong lemony and slight medicinal scents predominating.

*Lastingness of individual blooms.*—About 3 to 5 days, depending on temperature.

*Tepals.*—Number: About 3. Shape: Pointed oval, truncate at base. Size: Between about 4.0 cm to 4.5 cm long. Margin: Entire. Curvature: Slightly cupped. Arrangement: Whorled. Color: Ranging from Yellow-Green Group 150A to 150D.

Reproductive Organs:

*Androecium.*—Stamens: Number: About 85 per flower. Anther: Shape: Curved. Size: About 8 mm long, about 1 mm wide. Color: Near Yellow Group 4B at anthesis. Filament: Color: Near Yellow Group 4B at anthesis. Pollen Amount: Not measured. Pollen color: White. *Gynoecium.* Pistil Length: Between 2 mm to 3 mm. Stigma Color: Near White. Style Color: Near Yellow-Green Group 144A. Ovary Color: Near Yellow-Green Group 144B. Fruit/Seed: None yet observed.

I claim:

1. A new and distinct plant of *Magnolia virginiana* var. *australis* of the variety substantially as shown and described.

* * * * *